(12) United States Patent
Peery et al.

(10) Patent No.: US 12,326,200 B2
(45) Date of Patent: Jun. 10, 2025

(54) CENTRIFUGAL CASSETTE WITH MOLDED INSERTABLE VALVES

(71) Applicant: Terumo BCT, Inc., Lakewood, CO (US)

(72) Inventors: Randy Peery, Lakewood, CO (US); James Ladtkow, Broomfield, CO (US); Jesse Janzen, Golden, CO (US); Andrew Gloor, Lakewood, CO (US); Kevin Klimek, Denver, CO (US)

(73) Assignee: Terumo BCT, Inc., Lakewood, CO (US)

( * ) Notice: Subject to any disclaimer, the term of this patent is extended or adjusted under 35 U.S.C. 154(b) by 973 days.

(21) Appl. No.: 17/430,434

(22) PCT Filed: Feb. 26, 2020

(86) PCT No.: PCT/US2020/019914
§ 371 (c)(1),
(2) Date: Aug. 12, 2021

(87) PCT Pub. No.: WO2020/180563
PCT Pub. Date: Sep. 10, 2020

(65) Prior Publication Data
US 2022/0112967 A1 Apr. 14, 2022

Related U.S. Application Data

(60) Provisional application No. 62/812,666, filed on Mar. 1, 2019.

(51) Int. Cl.
*F16K 99/00* (2006.01)
*A61M 1/36* (2006.01)
(Continued)

(52) U.S. Cl.
CPC ..... *F16K 99/0011* (2013.01); *A61M 1/36226* (2022.05); *A61M 1/362262* (2022.05);
(Continued)

(58) Field of Classification Search
CPC ............. F16K 99/0011; F16K 99/0036; F16K 2099/0078; F16K 2099/0084;
(Continued)

(56) References Cited

U.S. PATENT DOCUMENTS 6,102,897 A * 8/2000 Lang ..................... F16K 13/00
604/246
2008/0187474 A1* 8/2008 Park ..................... F16K 99/0001
422/292
(Continued)

FOREIGN PATENT DOCUMENTS

BR 112015026232 B1 * 2/2022 ............ A61M 1/101

*Primary Examiner* — Walter D. Griffin
*Assistant Examiner* — Shuyi S. Liu
(74) *Attorney, Agent, or Firm* — Harness, Dickey & Pierce, P.L.C.

(57) ABSTRACT

Provided is a centrifuge cassette assembly (800) for separating a fluid and related method of manufacture. The cassette assembly includes a first chamber, a second chamber (308), a fluidic channel (808) creating a fluid connection between the first chamber and the second chamber, at least one molded insertion valve (600, 700) configured to control the flow of fluid in the fluidic channel and a heating element (802) for actuating the at least one molded valve. Further provided are Normally Open Valves (NOVs) (700) and Normally Closed Valves (NCVs) (600) which are capable of insertion into, and which control the fluid flow of, the centrifuge cassette assembly.

22 Claims, 10 Drawing Sheets

(51) Int. Cl.
  *B04B 5/04* (2006.01)
  *B29C 45/00* (2006.01)
  *B29K 23/00* (2006.01)
  *B29L 31/00* (2006.01)
  *G01N 35/00* (2006.01)

(52) U.S. Cl.
  CPC ..... *A61M 1/362265* (2022.05); *B04B 5/0442* (2013.01); *B29C 45/0053* (2013.01); *B29K 2023/083* (2013.01); *B29L 2031/7506* (2013.01); *F16K 99/0036* (2013.01); *F16K 2099/0078* (2013.01); *F16K 2099/0084* (2013.01); *G01N 2035/00495* (2013.01)

(58) Field of Classification Search
  CPC ............... F16K 99/0032; F16K 99/004; F16K 99/0044; F16K 99/0063; F16K 99/003; A61M 1/36226; A61M 1/362262; A61M 1/362265; A61M 2205/128; A61M 2205/3653; A61M 1/029; A61M 1/3693; B04B 5/0442; B29C 45/0053; B29K 2023/083; B29L 2031/7506; G01N 2035/00495; G01N 33/491; B01L 3/502707; B01L 2300/1827; B01L 2400/0677; B01L 3/502738
  See application file for complete search history.

(56) References Cited

U.S. PATENT DOCUMENTS

| | | | |
|---|---|---|---|
| 2009/0035847 A1* | 2/2009 | Cho | .................... B01F 35/7547 |
| | | | 435/289.1 |
| 2015/0014369 A1* | 1/2015 | Hatton | .................... F16K 21/04 |
| | | | 29/890.12 |

* cited by examiner though of the present application.

CENTRIFUGAL CASSETTE WITH MOLDED INSERTABLE VALVES

CROSS-REFERENCE TO RELATED APPLICATIONS

This application claims priority to U.S. Provisional Patent Application No. 62/812,666 filed Mar. 1, 2019, entitled "Centrifugal Cassette with Molded Insertion Valves," which is incorporated by reference herein in its entirety.

BACKGROUND

The present application describes a centrifugal cassette including molded Normally Open Valves (NOVs) and Normally Closed Valves (NCVs). The centrifugal cassette is configured to allow for insertion of the valves after the cassette has been partially manufactured in a hot plate welding process.

In the medical field, a centrifuge cassette or cartridge may be used to separate human or animal blood. Within the centrifuge cassette exist several fluid chambers connected by a variety of fluid channels operating together under centrifugal force to control the separation process. The flow of fluid in the fluid channels may be regulated by the actuation of NOVs and NCVs which typically include wax elements that are formed into the fluid channels of the centrifuge cassette during its manufacture. Such a cassette is disclosed in U.S. patent application Ser. No. 15/719,224, entitled "Centrifugal Fluid Separation Device," filed Sep. 28, 2017 by Terumo BCT, Inc.

Problematically, the incorporation of wax elements into the valves during manufacture of the cassette limits the number of methods by which the cassette may be manufactured. For example, although hot plate welding is a preferred manufacturing method for is cost and efficiency advantages, hot plate welding is generally not feasible because wax elements in the valves deform or are otherwise compromised under the heat and pressure of the welding process. For these and other reasons, there exists a need to improve valve and cassette construction. More particularly, a need exists to create valves capable of use in cassettes having sterile fluidic channels and which operate within a high G-field, yet which are also compatible with hot plate welding.

Embodiments of the present application have been made in view of these and other considerations. However, the relatively specific problems discussed above do not limit the applicability of the embodiments of the present application.

SUMMARY

The summary is provided to introduce aspects of some embodiments of the present application in a simplified form and is not intended to comprise and exhaustive list of all critical or essential elements of the claimed invention, nor is it intended to limit the scope of the claims.

According to one aspect of the present application, a Normally Closed Valve (NCV) for insertion into a fluidic channel is provided. The NCV includes at least one interference seal member, at least one valve seal post, and a valve rib. The at least one interference seal member is configured to cooperate with at least one interference seal member of a valve seat of a fluidic channel.

According to another aspect of the present application, a Normally Open Valve (NOV) for insertion into a fluidic channel is provided. The NOV includes at least one interference seal member and a lumen. The at least one interference seal member is configured to cooperate with at least one interference seal member of a valve seat of fluidic channel.

According to yet another aspect of the present application, a centrifuge cassette for separating a fluid is provided. The cassette includes a first chamber, a second chamber, a fluidic channel creating a fluid connection between the first chamber and the second chamber, at least one molded insertion valve configured to control the flow of fluid in the fluidic channel, and a heating element for actuating the at least one molded valve.

According to a further aspect of the present application, a method of manufacturing a centrifuge cassette assembly is provided. The method includes injection molding a first plate, the first plate including an upper valve seat, injection molding a second plate, the second plate including a fluidic channel and a lower valve seat, nesting each of the first plate and the second plate in a holding fixture, heating elements of the first plate and the second plate, aligning the valve seat of the first plate with the valve seat of the second plate, pressing the first plate and the second plate together, joining the plates, and inserting a valve into the joined plates, the valve engaging each of the upper valve seat of the first plate and the lower valve seat of the second plate.

Further embodiments of the present application include various devices, systems and methods related to centrifuge cassettes and molded insertion valves.

BRIEF DESCRIPTION OF THE DRAWINGS

Non-limiting and non-exhaustive embodiments are described with reference to the following figures.

DETAILED DESCRIPTION

The principles described in the present application may be further understood by reference to the following detailed description and the embodiments depicted in the accompanying drawings. Although specific features are shown and described below with respect to detailed embodiments, the present application is not limited to the embodiments described below. More particularly, embodiments may be described with respect to opening and closing sterile, microfluidic channels containing composite fluids under centrifugal force; however, such descriptions are merely illustrative, and those of skill in the art will appreciate that the embodiments are not limited to the descriptions herein. Embodiments described herein may be capable of use in products, processes, devices, and systems used to open and close fluid channels in any suitable application. Accordingly, the present application is not limited to the opening and closing of fluid channels in a centrifugal field.

Throughout this disclosure, the term "cassette half" may be interchanged with the term "cassette plate," and the term "cassette" may be used interchangeably with the term "cartridge."

Many of the various components of centrifuge systems are known in the art and are described in U.S. patent application Ser. No. 15/719,224, entitled "Centrifugal Fluid Separation Device," filed Sep. 28, 2017 by Terumo BCT, Inc., which is incorporated herein by reference in its entirety.

Figure 1:
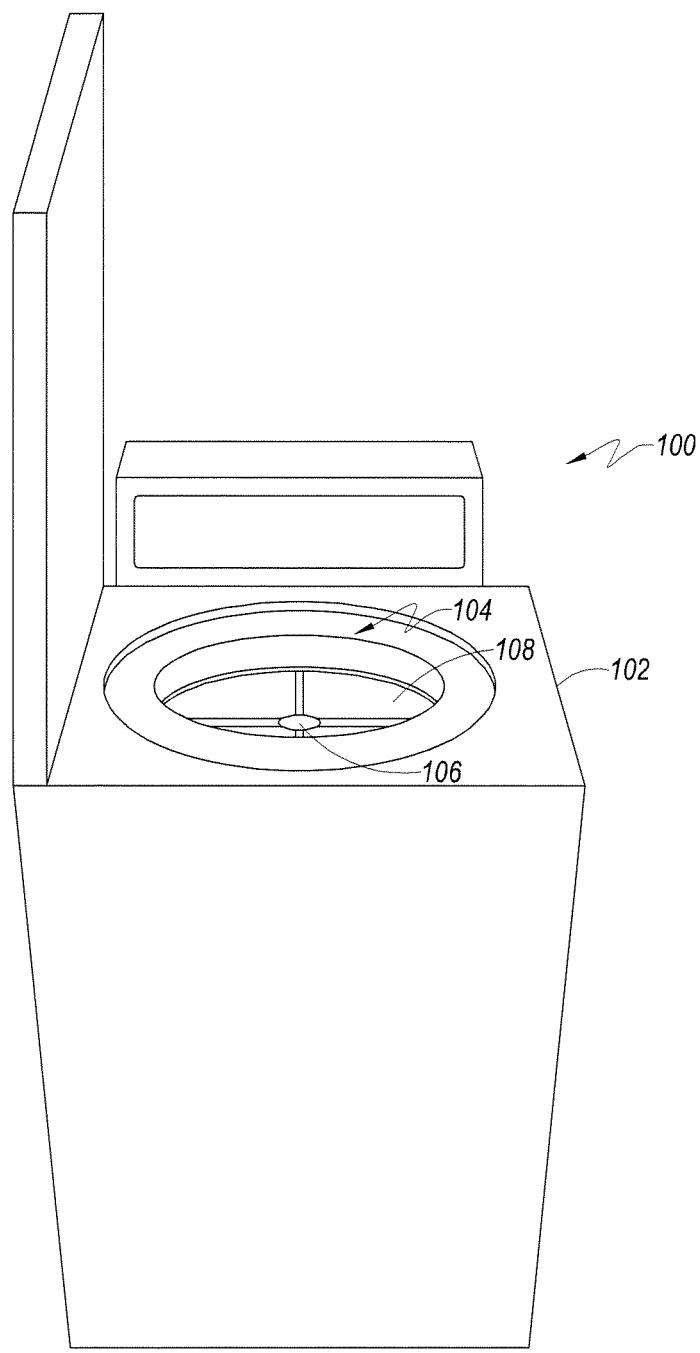
FIG. 1 illustrates a fluid separation system according to the related art.

FIG. 1 illustrates a fluid separation system according to the related art.

Referring to FIG. 1, a fluid separation system 100 includes a floor standing-type centrifuge 102; a rotor assembly 104 configured to be rotated by a motor about an axis of rotation 106; and at least one modular fluid separation cassette 108 affixed to the rotor assembly 104. The components of fluid separation system 100 together define a sterile and disposable fluid separation system.

As shown in FIG. 1, the centrifuge 102 is a floor standing-type centrifuge. The centrifuge 102 is capable of housing one or more modular fluid separation cassettes 108 of varying volumes and may be suitable for fluid separation of a higher volume than a benchtop-type or other small-scale centrifuge. For example, the floor-standing centrifuge 102 may be capable of housing one or more modular fluid separation cassettes 108 which may each be configured to separate from 1 ml to 300 ml of whole blood. More particularly, embodiments may be capable of separating between 10 ml and 125 ml of whole blood.

Figure 2:
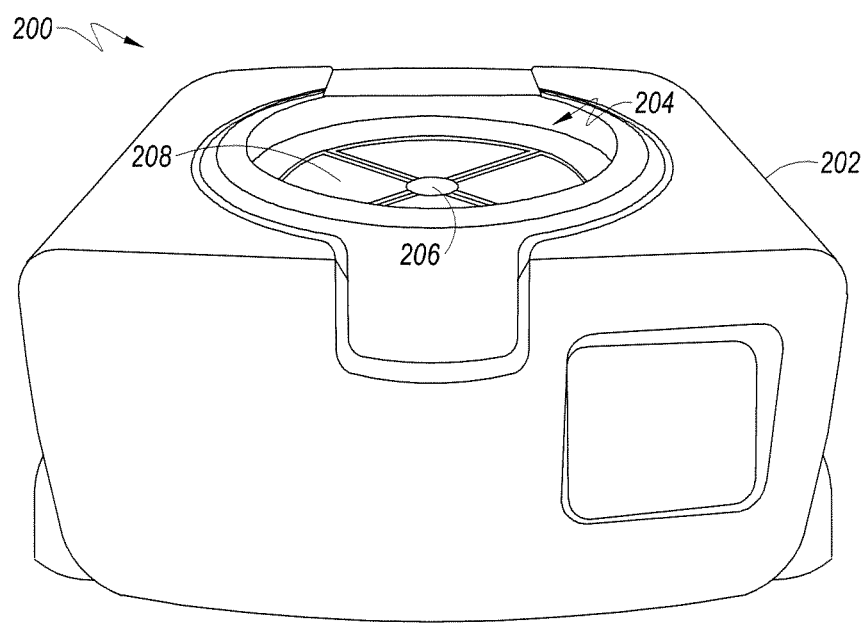
FIG. 2 illustrates another fluid separation system according to the related art.

FIG. 2 illustrates another fluid separation system according to the related art.

Referring to FIG. 2, the fluid separation system 200 includes a benchtop-type centrifuge 202; a rotor assembly 204 configured to be rotated by a motor about an axis of rotation 206; and at least one modular fluid separation cassette 208 affixed to the rotor assembly 204. The components of fluid separation system 200 together define a sterile and disposable fluid separation system.

Examples of suitable bench top-type centrifuges, such as that depicted in FIG. 2, are common and can be found throughout the art. In embodiments, the bench top-type centrifuge 202 may be capable of housing cassettes 208 of varying volumes and may be suitable for the separation of samples having a lower volume than the volume of samples suitable in a floor standing-type centrifuge 102 or other centrifuge. For example, the benchtop-type centrifuge 202 may be capable of housing one or more cassettes 208 which may each be configured to separate between 1 ml and 125 ml of whole blood. More particularly, embodiments may capable of separating between 10 ml and 60 ml of whole blood.

The fluid separation systems of FIGS. 1 and 2 are generally known in the art. In either system, various system components may include electronic control means and electronic communication means. For example, any of the centrifuge, the components of the rotor assembly or the cassettes may include any of one or more processors, embedded code, integrated hardwiring or circuitry, embedded sensors, or any other electronic means which may allow for one-way or for bi-directional wired or wireless communication, and which may allow for monitoring, assessment and control of system components. The present application proposes novel cassette components and novel Normally Open Valves (NOVs) and Normally Closed Valves (NCVs) to substitute for, or to compliment, what is known in the art.

Figure 3:
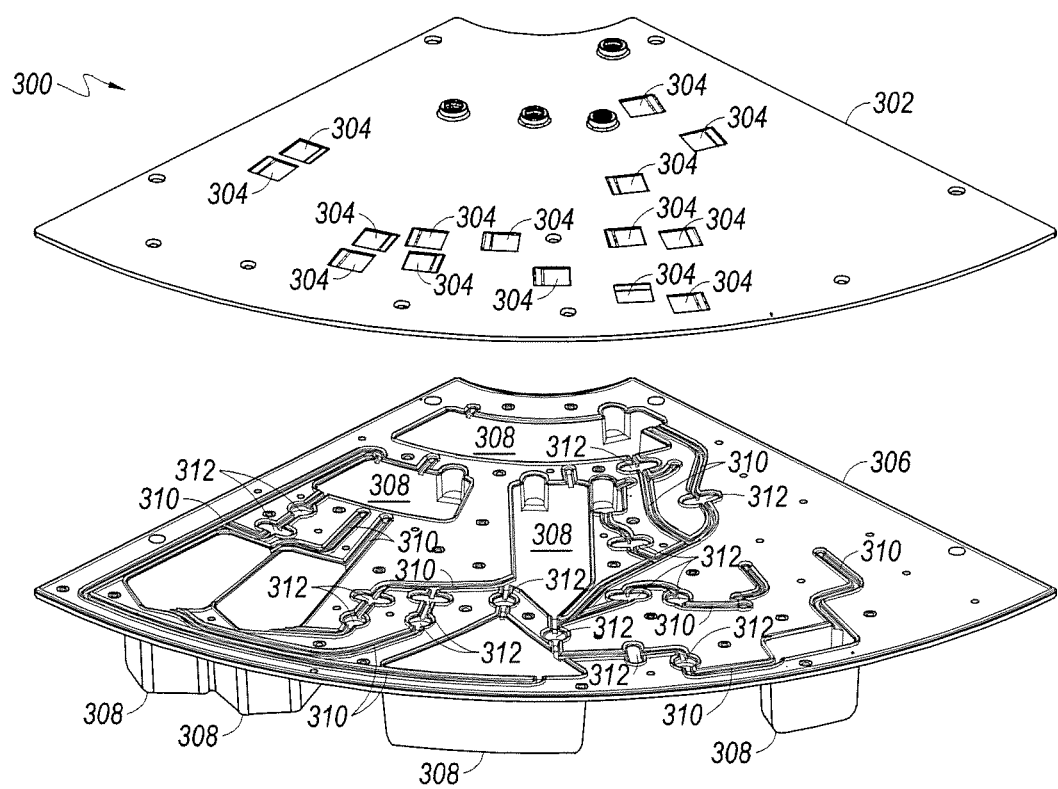
FIG. 3 is an exploded view of a centrifuge cassette assembly according to an embodiment of the present application.

FIG. 3 is an exploded view of a partial centrifuge cassette assembly according to the related art.

Referring to FIG. 3, partial centrifuge cassette assembly 300 comprises cassette top plate 302, including resistor insertion basins 304; and cassette bottom plate 306, including fluidic chambers 308, fluidic channels 310 and valve insertion voids 312.

Cassette top plate 302 and cassette bottom plate 306 are prefabricated. Each of top and bottom plate 302,306 is made of a thermoplastic material. In preferred embodiments, plates 302,306 comprise polypropylene and are produced in an injection molding process. The prefabricated plates 302, 306 are preferably fitted together using a hot plate welding process. Once the plates 302, 306 are fitted together, NOVs and NCVs according to embodiments of this application are inserted into valve insertion voids 312. Resistor insertion basins 304 in top plate 302 are configured to receive resistors (not shown) used to actuate the valves, and accordingly correspond to the location of the valve insertion voids 312 in cassette bottom plate 306. Among additional assembly components not shown in FIG. 3 are a resistor array including resistors placed in resistor insertion basins 304 and, optionally, a liquid impermeable layer or treatment applied to the cassette bottom plate in order to prohibit an ingress and egress of unwanted fluid into the cassette. Such additional layers or treatments are incorporated into the cassette assembly after the hot plate welding process is complete.

In operation, the centrifuge cassette assembly is loaded with a fluid, such as blood or a blood product, and spun in a centrifuge. As the cassette spins, centrifugal force causes the fluid in the cassette to flow outward (i.e., downhill) in the G-field and separate. The position of fluidic chambers and fluidic channels throughout the cassette determine the flow of fluid under centrifugal force. Accordingly, the processing of the cassette, including the speed and timing of the centrifuge, is determined based on the relative size of the cassette and the relative sizes, positions and geometries of its various fluidic chambers and channels. Processing likewise depends upon the components and characteristics of the fluid to be separated. In the case of human or animal whole blood, the cassette may be designed to separate the whole blood into plasma, Red Blood Cells (RBCs), White Blood Cells (WBCs) and platelets.

As fluid flows through the cassette under centrifugal force, the fluidic channels must remain sterile, yet must also include means by which the fluid can be reliably controlled. Fluid control is accomplished using embodiments of the Normally Open Valves (NOVs) and Normally Closed Valves (NCVs) described throughout this application. NOVs and NCVs described herein are designed to be inserted into the cassette assembly after the cassette halves have been joined in the hot plate welding process. In certain embodiments, a single NOV or NCV may be positioned in a fluid channel, whereas a combination of NCVs and NOVs may be positioned in a fluidic channel in other embodiments. The latter configuration allows the fluidic channel to be both opened and closed. For instance, fluid may be initially held in position by an NCV which is then actuated causing fluid to flow through the channel. The channel may subsequently be closed by actuation of an NOV.

In preferred embodiments, the individual top and bottom cassette halves 302,306 are produced in an injection molding process; however, the method of manufacturing of the plates is not limited. Various alternative manufacturing methods include, but are not limited to, compression molding, thermoforming, three-dimensional printing or any other suitable manufacturing method.

The base materials chosen for the manufacture of the top and bottom cassette plates is similarly not limited and may include any of several thermoplastic polymers such as polypropylene, polystyrene, and the like. The cassette components may also be hydrophobic or may include a hydrophobic coating or a hydrophobic treatment. In various further embodiments, the cassette halves may be of a dissimilar material. For example, a polypropylene top cassette half may be joined with a mixed or non-polypropylene bottom cassette half.

As mentioned above, the top and bottom cassette plates are preferably joined in a hot plate welding process. Hot plate welding is highly precise, highly efficient and relatively inexpensive. Modern hot plate welding processes achieve rapid cycle time and consistent weld quality using reduced tooling. A further advantage of hot plate welding is the ability to join a variety of thermoplastic materials. Nonetheless, in further embodiments, alternative techniques may be used to join cassette plates, such as laser welding and ultrasonic welding.

In embodiments, cassettes described herein may be single use (i.e., disposable) or multiple use, and may be of a variety of types, sizes and configurations. For example, the cassettes described herein may take the form of a "wedge," or of a segment of a disk shape. In such embodiments, several cassettes together may form a complete disk shape. In other embodiments, a single cassette may take the form of an entire disk.

Figure 4:
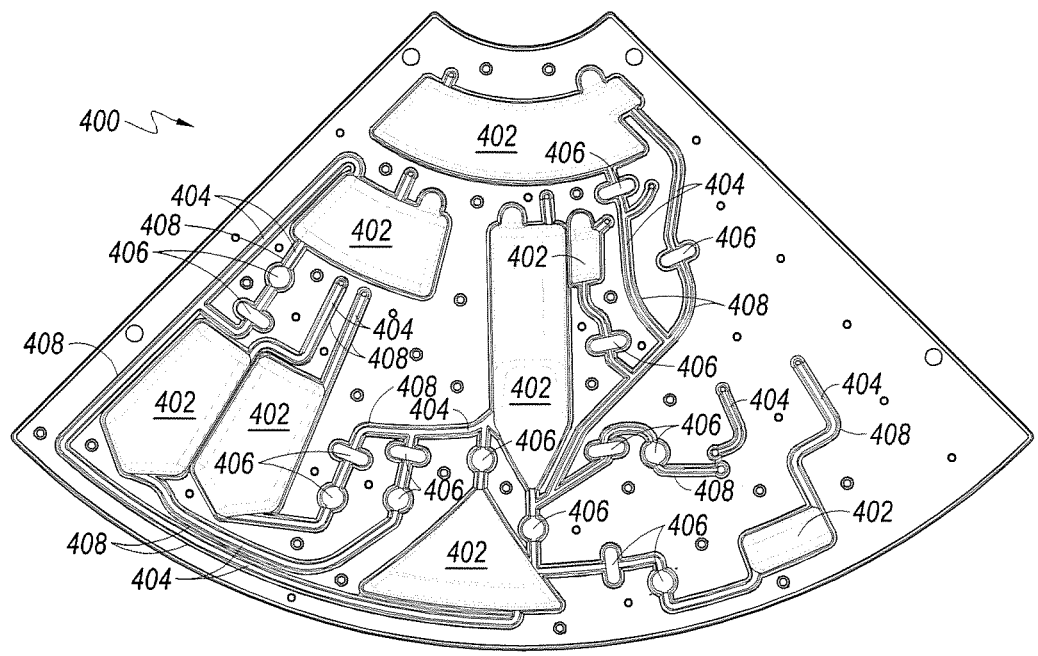
FIG. 4 is a plan view of a bottom plate of a centrifuge cassette assembly according to an embodiment of the present application.

FIG. 4 is a plan view of a bottom plate of a centrifuge cassette assembly according to an embodiment of the present application.

Referring to FIG. 4, the centrifuge cassette bottom plate 400 includes fluidic chambers 402; fluidic channels 404; valve insertion voids 406; and weld beads 408.

Fluidic chambers 402 are connected by fluidic channels 404. Fluidic channels 404 determine the path of fluid flow between fluidic chambers 402. Fluidic channels 404 incorporate valve insertion voids 406 including lower valve seats (shown below) into which insertion valves are respectively inserted and seated in the fluidic channel 404.

Figure 5:
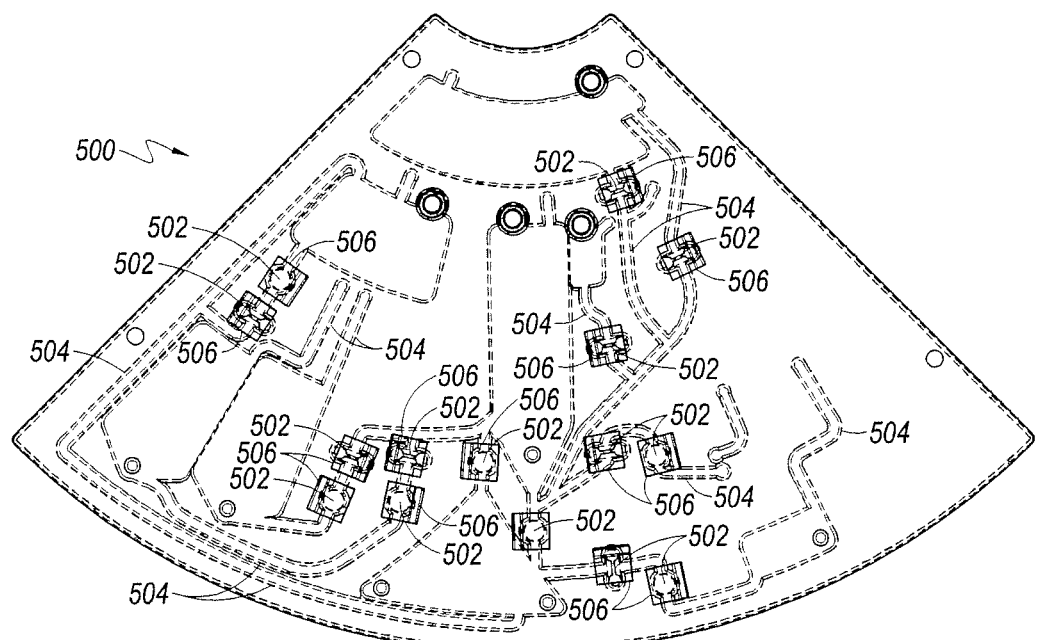
FIG. 5 is a plan view of a top plate of a centrifuge cassette assembly according to an embodiment of the present application.

Weld beads 408 are a deposit or an embankment of base material used to weld the bottom plate 400 and top plate (as shown in FIG. 5) together. As shown, the weld beads 408 essentially follow the contour of the fluidic chambers 402 and fluidic channels 404. During hot plate welding of cassette assembly, complementary weld beads on the top plate (as shown in FIG. 5) are heated and joined with molten base material from the weld beads 408 of the bottom plate.

FIG. 5 is a plan view of a top plate of a centrifuge cassette assembly according to an embodiment of the present application.

Referring to FIG. 5, the centrifuge cassette top plate 500 includes upper valve seats 502; weld beads 504; and resistor insertion basins 506.

Upper valve seats 502 are configured to slidably accept an end portion (i.e., an insertion portion) of an insertion valve once the cassette halves have been joined. That is, once the cassette halves are joined, insertion valves are inserted into valve insertion voids 406 of the lower cassette plate 400 shown in FIG. 4 and seated in each of lower valve seats (shown below) and upper valve seats 502. Proper seating of the valve is important for maintaining valve integrity under the high fluidic pressures in the fluid channel.

As with the bottom plate 400, the weld beads 504 of the top plate 500 essentially follow the contour of the fluidic channels 402 and chambers 404 of the bottom plate. That is, weld beads 504 of top plate 500 and weld beads 408 of bottom plate 400 are precisely positioned to align with one another to facilitate joining of the plates.

In various alternative embodiments of the plates 400, 500 shown in FIG. 4 and FIG. 5, excess molten base material from the cassette welding process may flow into a flash well or material displacement well (not shown) positioned adjacent to either or both of weld beads 408, 504. In preferred embodiments, the material displacement well exists between the weld beads and the adjacent fluidic channel or fluidic chamber. In this configuration, any excess weld material resulting from the joining of the cassette plates flows into the material displacement well and remains isolated from the fluid channels and chambers.

In yet further alternative embodiments, the position and form of the weld beads 408, 504 may vary. That is, although the weld beads 408, 504 will generally be deposited so as to contour the fluidic channels and chambers, the weld beads 408, 504 may take any form or be deposited in any manner desirable for the joining of the cassette plates. The position of displacement wells may vary accordingly.

Figure 6A:
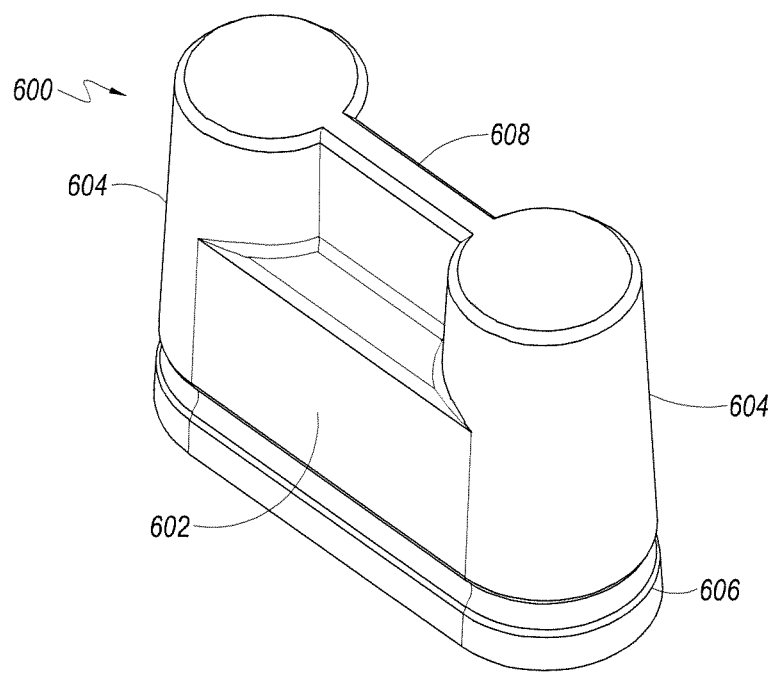
FIGS. 6A and 6B are alternative views of a Normally Closed Valve (NCV) according to an embodiment of the present application.
Figure 6B:
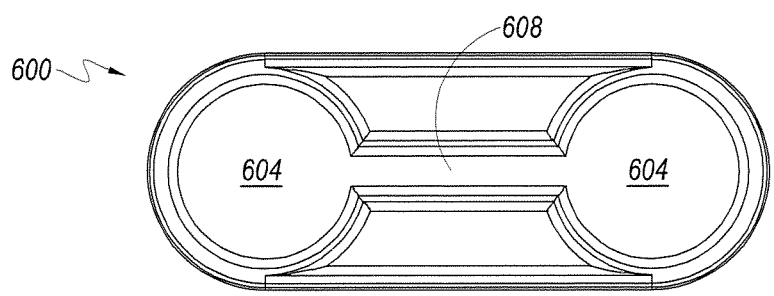

FIGS. 6A and 6B are alternative views of a Normally Closed Valve (NCV) according to an embodiment of the present application.

FIG. 6A is a perspective view of NCV 600. Referring to FIG. 6A, the NCV 600 comprises a valve base 602; seal posts 604; interference seal member 606; and a valve rib 608.

As shown in FIG. 6, the NCV is comprised of a valve base 602 and seal posts 604 supporting valve rib 608. Interference seal member 606 forms part of the valve base 602, as shown, and is configured to engage an interference seal member of the lower valve seat (shown below) positioned in the valve insertion void of the fluidic channel of the cassette bottom half. This engagement between interference seal members of the valve and the lower valve seat creates an interference seal capable of securing the bottom of the valve in the lower valve seat of the valve insertion void.

Notably, seal posts 604 extend upward from valve base 602 and taper toward the top of the NCV 600. These tapers form another aspect of valve geometry important in facilitating valve insertion and proper valve seating, and which further contribute to the securing of the valve in the fluidic channel. The top portions (i.e., insertion portions) of the seal posts 604 and valve rib 608 are configured to slidably engage the upper valve seat (shown below) in the top cassette plate. When properly seated, insertion portions or end portions of seal posts 604 are securely nested in the valve seat of the top plate, and valve rib 608 is oriented perpendicular to, and fully obstructs, the fluidic channel.

To actuate and open NCV 600, electrical energy is inputted into a resistor positioned in the top plate above the valve rib 608. Heat from the resistor causes the valve rib 608 to soften and fold, opening the channel and allowing fluid to flow.

In alternative embodiments, the design of NCV 600 is not limited. For instance, NCV 600 may assume any configuration that includes an actuatable rib sufficiently supported to withstand the high fluidic pressures associated with centrifugation (i.e., fluidic pressures of up to 120 PSI). In yet further embodiments, portions of the NCV 600 may be removed or otherwise configured to facilitate potting of the NCV 600 in the cassette assembly. In such embodiments, an adhesive may be used as potting material.

As shown in FIG. 6A, interference seal members 606 form an essentially semi-circular convex protrusion. This protruding interference seal member 606 is configured to cooperate with a complimentary interference seal member of a valve seat. The complimentary interference seal member includes an essentially semi-circular concave aspect configured to accommodate interference seal member 606. Upon insertion of the valve into the cassette, the complimentary interference seal members of the respective valve and valve insertion void essentially "snap" into place with one another. In embodiments, interference seal member configurations may vary, and may include a variety of geometries in either single or multiple seal configurations. Any chosen interference seal member configuration must be capable of securing the valve in the valve seat throughout operation and preventing an ingress or egress of fluid with respect to the fluid channel.

FIG. 6B is a top view of a NCV 600. Referring to FIG. 6B, NCV 600 comprises seal posts 604 and a valve rib 608.

When NCV 600 is properly inserted into a cassette, top portions (i.e., seating portions) of seal posts 604 and rib 608 are seated into the upper valve seat of the top plate and valve rib 608 is oriented perpendicular to the fluidic channel. Importantly, the seating portions of the seal posts 610 and valve rib 608 are seated deeply enough in the top plate to impart the structural integrity required for the valve to withstand the high fluidic pressures in the channel.

Figure 7A:
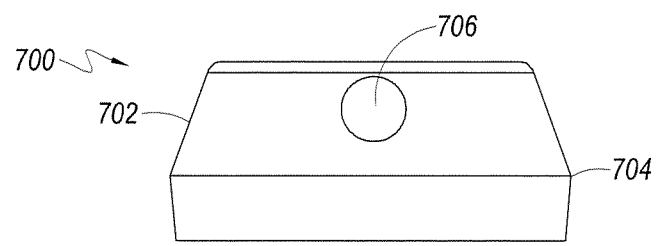
FIGS. 7A and 7B are alternative views of a Normally Open Valve (NOV) according to an embodiment of the present application.
Figure 7B:
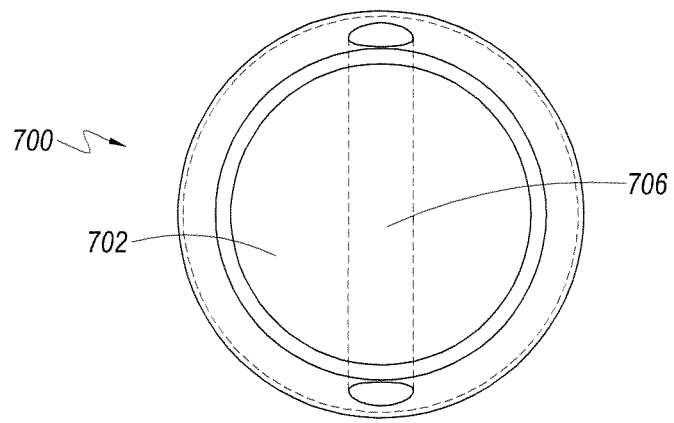

FIGS. 7A and 7B are alternative views of a Normally Open Valve (NOV) according to an embodiment of the present application.

FIG. 7A is a side view of a NOV 700. Referring to FIG. 7A, NOV 700 includes valve body 702, interference seal members 704; and a lumen 706.

As shown in FIG. 7A, valve 700 is essentially configured as an asymmetrical combination of two truncated cones. The portion of the valve body 702 having the largest diameter is the point of intersection of interference seal members 704. The bottom truncated conical portion of the valve 700 tapers gently inward toward the bottom of the valve 700. The top truncated conical portion of the NOV 700 tapers more aggressively inward toward the top of the NOV 700. This truncated, bi-conical valve configuration forms interference seal members 704 which cooperate with complimentary interference seal members in a lower valve seat of a valve insertion void to seat the NOV 700 in a fluidic channel of a centrifugal cassette.

When properly seated in the cassette, the top portion (i.e., an insertion portion) of the NOV 700 cooperates with an upper valve seat in the cassette top plate, and interference seal members 704 cooperate with complimentary interference seal members of the lower valve seat in the valve insertion void of the bottom plate. Lumen 706 is aligned with the fluidic channel, forming a continuous and unobstructed flow path in the fluidic channel. Proper seating of the NOV 700 causes the valve to securely "snap" into place.

To actuate and close the NOV, electrical energy is inputted into a resistor positioned in the top cassette plate above the lumen 704. Heat from the resistor causes NOV 700 material around the lumen 704 to become molten, collapsing and closing the valve.

In embodiments, NOV 700 design may vary. For instance, a NOV 700 may be configured to include irregular aspects more aggressive interference seal members, or to include a higher number of interference seal members. For instance, one or more of the tapered aspects of the NOV 700 may include a concave aspect. Interference seal members may optionally be further included in the top portion or seating portion of the NOV 700 and may cooperate with interference seal members of an upper valve seat. Lumen geometry 706 may also vary. For instance, a lumen having a different cross-sectional area or geometry, or a lumen including a different flow path may be incorporated into NOV 700. For instance, a valve configured to include a torturous fluidic flow path or a fluid flow path including a small cross section may be implemented to decrease flow rate. Alternative valve designs may similarly be implemented, for example, to improve aspects of valve actuation or reliability.

FIG. 7B is a top view of a NOV 700. Referring to FIG. 7B, NOV 700 includes valve body 702 and lumen 706.

When correctly inserted and seated in the cassette, the lumen 706 is aligned with the fluidic channel of the cassette, allowing the fluidic channel to remain unobstructed until actuation of the valve.

Preferably, the NCVs 600 and NOVs 700 are injection molded; however, in embodiments, NCVs 600 and NOVs 700 may be molded using alternative conventional methods. NCVs 600 and NOVs 700 are semi-rigid and made of an elastomeric material. The semi-rigidity of the valves, including the interference seal members, provides the valves with both sufficient flexibility to be inserted into the cassette and properly seat, and sufficient rigidity to maintain valve integrity under high fluidic pressure.

Examples of suitable valve materials include Ethylene Vinyl Acetate (EVA) wax and EVA blends. In embodiments, DuPont™ Elvax® 410 (ethyl-vinyl acetate copolymer resin) may be preferred. Such materials may exhibit a narrow or "sharp" melting point and favorable flexibility and surface adhesion. Other materials having characteristics similar to EVA may also be used.

Figure 8A:
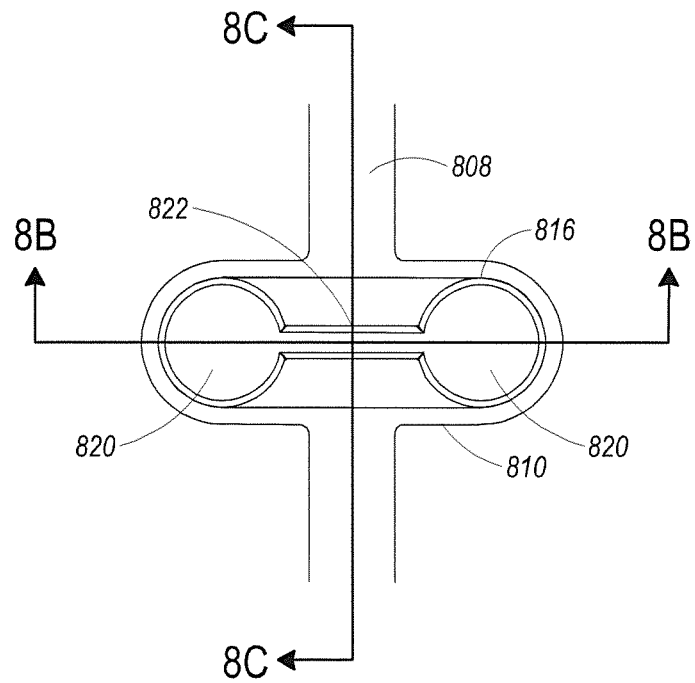
FIGS. 8A to 8C are alternative views of a NCV seated in a fluidic channel of a centrifuge cassette assembly according to an embodiment of the present application.
Figure 8B:
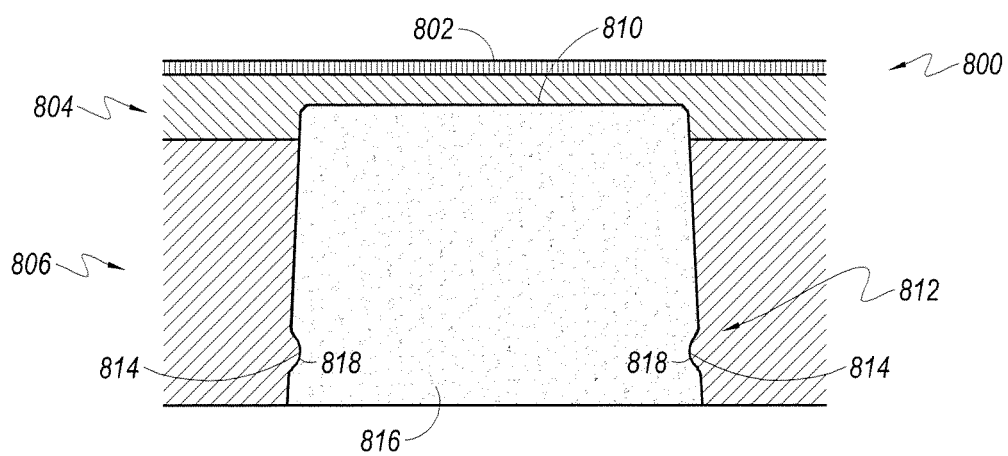
Figure 8C:
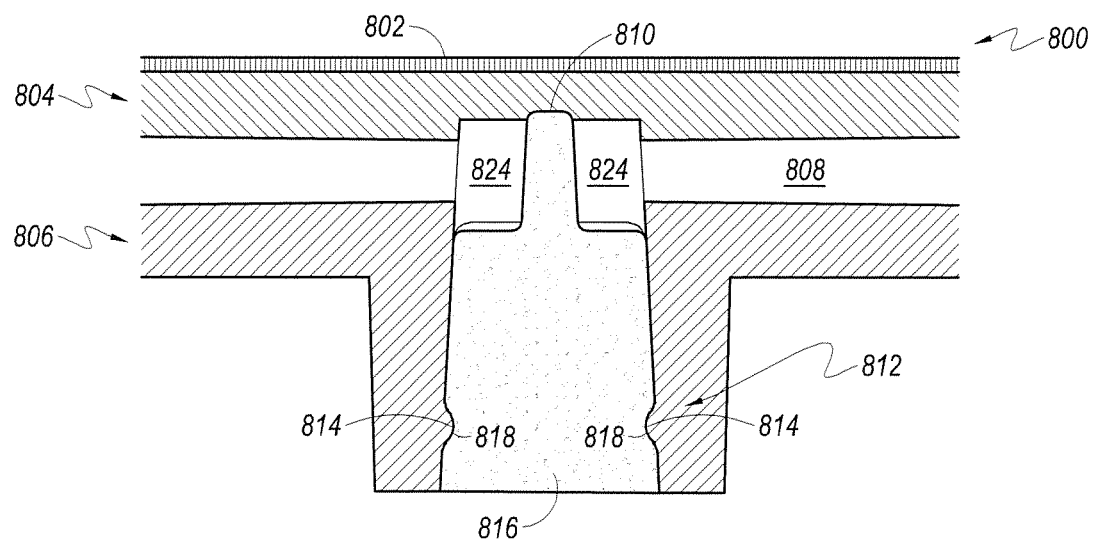

FIGS. 8A to 8C are alternative views of a cassette assembly including a Normally Closed Valve (NCV) seated in a fluidic channel of the cassette assembly according to an embodiment of the present application.

Referring to FIGS. 8A to 8C, the cassette assembly 800 includes a resistor layer 802; a top cassette plate 804; a bottom cassette plate 806; a fluidic channel 808, including an upper valve seat 810 and a lower valve seat 812, the lower valve seat 812 incorporating interference seal members 814; an NCV 816, including interference seal members 818; seal posts 820 and rib 822; and rib displacement zone 824.

FIG. 8A is a top view of the NCV 816 seated in a fluidic channel 808 of a centrifuge cassette assembly 800 of FIG. 8B. As shown in FIG. 8A, fluidic channel 808 includes concave recessions forming upper valve seat 810. Upper valve seat 810 is configured to receive and accommodate end portions of valve sealing posts 820 and rib 822 of NCV 816. The concave recessions of upper valve seat 810 surrounding end portions of the NCV 816 assist in securing the valve against the high fluidic pressures in the channel 808. The specific dimensions of the upper valve seat 810 generally conform to the geometry of the valve; however, in embodiments, the geometry of the valve seat 810 is not limited and any dimensions sufficient to secure the valve in place against the fluidic pressure in the channel 808 may suffice.

FIG. 8B is a cross-section view of cassette assembly 800 including NCV 816 seated in fluidic channel 808. As shown in FIG. 8B, top plate 804 and bottom plate 806 are in a joined state and NCV 816 has been inserted into the joined cassette halves. Interference seal members 818 of NCV 816 are cooperating with interference seal members 814 of lower valve seat 812 to secure NCV 816 in place. Upper valve seat 806 has received a seating portion or a top portion of sealing posts 820 and rib 822.

As shown, lower valve seat 812 is configured to compliment the geometry of NCV 816. In particular, interference seal members 814 of lower valve seat 812 act in cooperation with complimentary interference seal members 818 of the NCV 816 to securely seat the NCV 816 in the fluid channel. That is, the valves are mechanically pressed into the insertion void to engage interference seal members, causing the valve to "click" in place.

FIG. 8C is another cross-section view of cassette assembly 800 including NCV 816 seated in fluidic channel 808. As shown in FIG. 8C, a rib displacement zone 824 exists within the fluidic channel 808 on either side of the rib 822 of seated NCV 816. Rib displacement zone 824 provides a space for the deformed rib to rest once the NCV has been actuated. That is, actuation (i.e., heating) of NCV 816 allows for the fluidic pressures in the fluidic channel 808 to deform the malleable rib 822, forcing it downward by the flow of fluid. As the rib 822 is forced into the rib displacement zone 824, obstruction of the fluid channel 808 by the rib is avoided. In embodiments, the specific design and exact dimension of the rib displacement zone 824 is not limited; any rib displacement zone 824 providing a space for actuated rib 822 to rest without obstructing fluid channel 808 may be incorporated. In certain embodiments, a single rib displacement zone 824 may exist in the fluid channel 808 only on the downhill side of, or downstream of, valve rib 822.

As shown in both FIGS. 8B and 8C, resistor layer 802 is included in the cassette assembly. The resistor layer 802 is adhered to the top of the top plate 804 and includes a resistor positioned above the upper valve seat 810 such that, upon the inputting of sufficient electrical energy, the valve 816 will actuate.

In further embodiments, a liquid impermeable layer may be adhered to the bottom of the bottom plate 806 to prevent liquid ingress and egress into fluid channel 808 by way of cooperating interference seal members 814, 818.

Figure 9A:
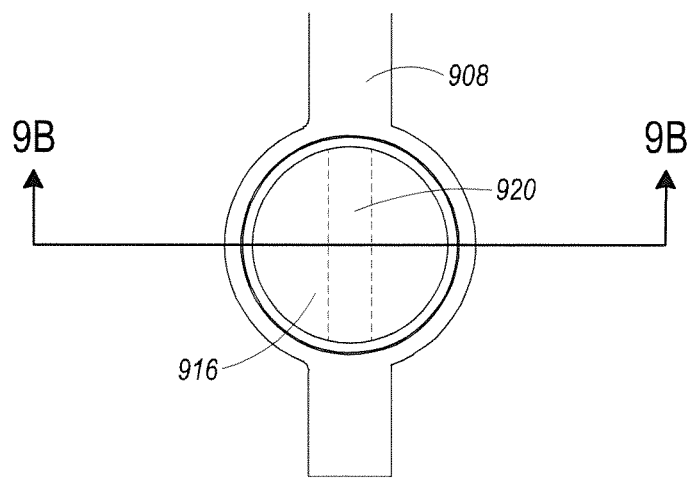
FIGS. 9A and 9B are alternative views of a NOV seated in a fluidic channel of a centrifuge cassette assembly according to an embodiment of the present application.
Figure 9B:
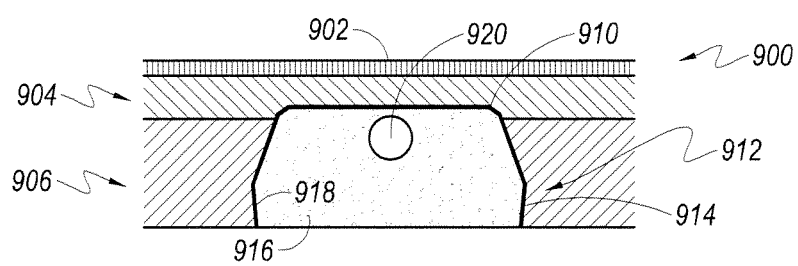

FIGS. 9A and 9B are alternative views of a NOV seated in a fluidic channel of a centrifuge cassette assembly according to an embodiment of the present application.

Referring to FIGS. 9A and 9B, the cassette assembly 900 includes a resistor layer 902; top cassette plate 904; bottom cassette plate 906; a fluidic channel 908, including an upper valve seat 910 and a lower valve seat 912, the lower valve seat incorporating interference seal members 914; and a NOV 916, including interference seal members 918 and a lumen 920.

FIG. 9A is a top view of the NOV 916 seated in a fluidic channel of a centrifuge cassette assembly 900 of FIG. 9B. As shown in FIG. 9A, fluidic channel 908 includes concave recessions forming upper valve seat 910. Upper valve seat 910 is configured to receive and accommodate an end portion of NOV 916. The concave recessions of upper valve seat 910 surround an end portion of the NOV 910 and assist in securing the NOV 910 against the high fluidic pressures in the channel 908. The specific dimensions of the upper valve seat 910 generally conform to the geometry of the NOV; however, in embodiments, the geometry of the upper valve seat 910 is not limited and any dimensions sufficient to secure the valve in place against the fluidic pressure in the channel 908 may suffice.

FIG. 9B is a cross-section view of cassette assembly 900 including NOV 916 seated in fluidic channel 908. As shown in FIG. 9B, top plate 904 and bottom plate 906 are in a joined state and NOV 916 has been inserted into the joined cassette halves. Interference seal members 914 of NOV 916 are cooperating with interference seal members 918 of lower valve seat 912 to secure NOV 916 in place. Upper valve seat 910 has received a seating portion or a top portion of NOV 916.

As shown, lower valve seat 912 is configured to compliment the geometry of NOV 916. In particular, interference seal members 914 of lower valve seat 912 act in cooperation with complimentary interference seal members 918 of the NOV 916 to securely seat the NOV 916 in the fluid channel 908. That is, the valves are mechanically pressed into the insertion void to engage interference seal members, causing the valve to "click" in place.

The resistor layer 902 is adhered to the top of the top plate 904 and includes a resistor positioned above the upper valve seat 910 such that, upon the inputting of sufficient electrical energy, the valve 916 will actuate. Placement of the resistor, and the resistor insertion basins, requires a position that is sufficiently proximate to the valve for adequate heating and resultant valve actuation, yet sufficiently distant from the valve to allow the valve seating portions to seat deeply in the cassette top plate.

In further embodiments, a liquid impermeable layer may be adhered to the bottom of the bottom plate 906 to prevent liquid ingress and egress into fluid channel 908 by way of cooperating interference seal members 914, 918.

Notably, in most cases, the NOVs and NCVs described in the various embodiments herein are inserted into the cassette assembly post hot-plate weld at the time of cassette manufacture. However, in embodiments, NOVs and NCVs may be inserted at a later point before the cassette is placed in service.

Figure 10:
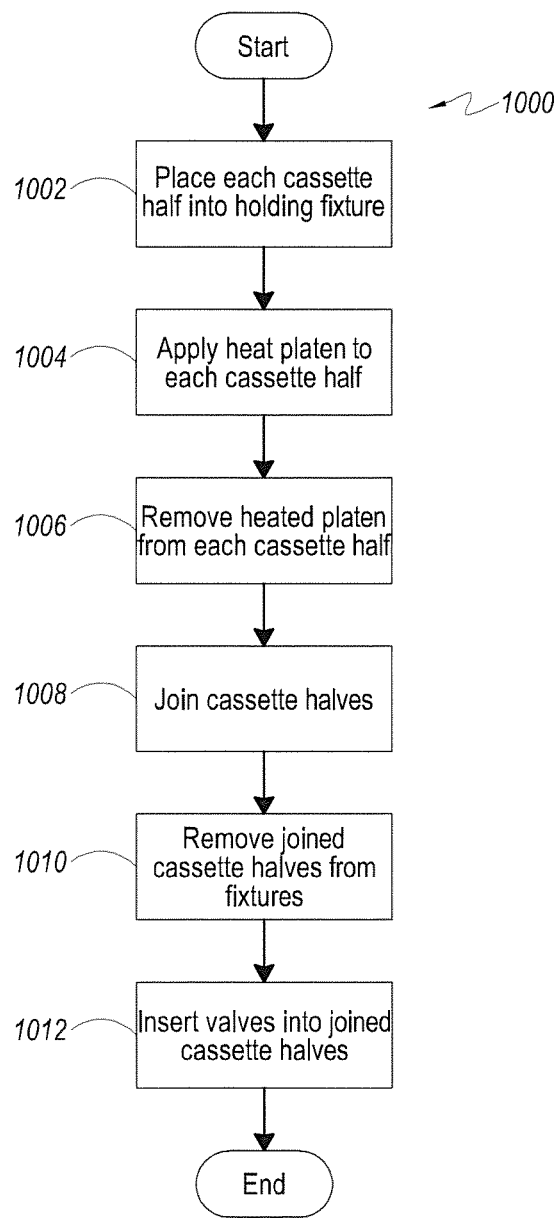
FIG. 10 is a flow diagram illustrating a method of manufacturing a valve assembly according to an embodiment of the present application.

FIG. 10 illustrates a flow diagram of a method of manufacturing a partial cassette assembly according to an embodiment of the present application.

Referring to FIG. 10, the process begins in step 1002 as each prefabricated thermoplastic cassette half (as shown in FIG. 3) is nested in a holding fixture. Next, in step 1004, joining surfaces of each cassette half are subjected to a heat plate of a heated platen for a predetermined period. Next, in step 1006, once the joining surfaces of each cassette half reach molten temperature, the plate and platen are removed. Next, in step 1008, the holding fixtures are pressed together, forcing the molten joining surfaces of the two halves to contact one another, forming a permanent bond. Next, in step 1010, once the bond formed between the two halves has cooled, the joined cassette halves are removed from the fixtures. Next, in step 1012, insertion valves are inserted into valve insertion voids and seated in valve seats.

After the hot plate welding of the top and bottom cassette halves, a resistor layer or resistor array including resistors for actuating the valves is adhered to the top of the joined cassette halves. Optionally, as mentioned above, a liquid impermeable layer is also applied to the bottom of the joined cassette halves. Further cassette components may optionally be added to complete the cassette assembly.

In various embodiments, operation of the cassette assembly or its individual components may be controlled by one or more processors included therein and may advantageously comprise a plurality of embedded computer processors that are part of a computer system. The computer system may also include components that allow a user to interface with the computer system, including for example, memory and storage devices (RAM, ROM (e.g., CD-ROM, DVD), magnetic drives, optical drives, flash memory,); communication/networking devices (e.g., wired such as modems/network cards, or wireless such as Wi-Fi); input devices such keyboard(s), touch screen(s), camera(s), and/or microphone(s); and output device(s) such as display(s), and audio system(s). To assist the operator of the centrifuge cassette assemblies described herein with various aspects of operation, such embodiments may include a graphical user interface with a display that includes an interactive touch screen.

Notwithstanding the various embodiments specifically enumerated throughout this disclosure, those skilled in the art will appreciate that a variety of modifications and optimizations could be implemented for particular applications. It is to be understood that this application is not limited to any specific configuration described herein. For instance, fluidic channels may include a variety of valves or valve combinations, including both insertion and non-insertion valves. Likewise, the number of valves may be adjusted for a particular application. Additionally, the present application is not limited to the separation of blood. That is, the principles of the present application may be applicable to the separation or removal of one or more specific constituent from many composite fluids. Accordingly, various modifications and changes may be made in the arrangement, operation, and details of the methods and systems of the present application which will be apparent to those skilled in the art.

What is claimed is:

1. A Normally Closed Valve (NCV) for insertion into a fluidic channel, the NCV comprising:
   a valve base including at least one interference seal member;
   a pair of valve seal posts; and
   an elongated valve rib that extends between and connects the pair of valve seal posts, and is configured to seal the fluidic channel when the NCV is inserted therein;
   wherein the at least one interference seal member is configured to cooperate with at least one interference seal member of a valve seat.

2. The NCV of claim 1, wherein the valve seal posts are tapered.

3. The valve of claim 1, wherein the valve comprises Ethylene Vinyl Acetate (EVA).

4. A Normally Open Valve (NOV) for insertion into a fluidic channel, the NOV comprising:
   a valve base including a first truncated cone section having a first base connected to a second of a second connected cone section, the connection between the first base and the second base of the first and second truncated cone sections defining an interference seal member; and
   a lumen;
   wherein the interference seal member is configured to cooperate with at least one interference seal member of a valve seat.

5. The NOV of claim 4, wherein the valve includes at least one truncated conical feature.

6. The valve of claim 4, wherein the valve comprises Ethylene Vinyl Acetate (EVA).

7. A centrifuge cassette assembly for separating a fluid, the cassette assembly comprising:
   a first chamber;
   a second chamber;
   a fluidic channel creating a fluid connection between the first chamber and the second chamber;
   a molded insertion valve configured to control the flow of fluid in the fluidic channel; and
   a heating element for actuating the molded insertion valve,
   wherein the molded insertion valve includes either a normally closed valve (NCV) or a normally open valve (NOV),
   wherein the normally closed valve (NCV) includes a first valve base including at least one first interference seal member; a pair of valve seal posts; and an elongated valve rib that extends between and connects the pair of valve seal posts, and is configured to seal the fluidic channel; wherein the at least one first interference seal member is configured to cooperate with at least one interference seal member of a valve seat; and
   wherein the normally open valve (NOV) includes a second valve base including a first truncated cone section having a first base connected to a second base of a second connected cone section, the connection between the first base and the second base of the first and second truncated cone sections defining a second interference seal member; and a lumen, wherein the second interference seal member is configured to cooperate with the at least one interference seal member of the valve seat.

8. The cassette assembly of claim 7, wherein the lumen has a same cross-sectional geometry as a portion of the fluidic channel.

9. The cassette assembly of claim 7, wherein the molded insertion valve comprises Ethylene Vinyl Acetate (EVA).

10. The cassette assembly of claim 7, wherein the cassette further comprises at least one valve seat in a bottom portion of the fluidic channel, the valve seat configured to accept a bottom portion of the molded insertion valve.

11. The cassette assembly of claim 10, wherein the cassette further comprises at least one valve seat in a top portion of the fluidic channel, the valve seat configured to accept a top portion of the molded insertion valve.

12. The cassette assembly of claim 10, wherein the valve seat in the bottom portion of the fluidic channel comprises at least one interference seal member configured to cooperate with either the first interference seal member of the NCV or the second interference seal member of the NOV.

13. The cassette assembly of claim 7, further comprising a resistor layer including at least one resistor.

14. The cassette assembly of claim 7, further comprising a liquid impermeable layer.

15. A method of manufacturing a centrifuge cassette assembly, the method comprising:
   injection molding a first plate, the first plate including an upper valve seat;
   injection molding a second plate, the second plate including a fluidic channel and a lower valve seat;
   nesting each of the first plate and the second plate in a holding fixture;
   heating elements of the first plate and of the second plate;
   aligning, with one another, the upper valve seat and the lower valve seat; pressing the first plate and the second plate together, joining of the plates; and
   inserting a valve into the joined plates, the valve engaging each of the upper valve seat and the lower valve seat; and
   adhering, to the cassette, a resistor layer that is configured to melt a material of the valve.

16. The method of claim 15, further comprising applying, to the cassette, a liquid impermeable layer.

17. The method of claim 15, wherein the valve is a Normally Open Valve (NOV).

18. The method of claim 15, wherein the valve is a Normally Closed Valve (NCV).

19. The method of claim 15, wherein the valve is made of EVA (Ethylene-vinyl acetate).

20. The method of claim 15, wherein the valve is produced in by an injection molding process.

21. The method of claim 15, wherein the valve includes interference seal members.

22. The method of claim 15, wherein the lower valve seat includes at least one interference seal member.

\* \* \* \* \*